US012620639B2

(12) United States Patent
Zhang et al.

(10) Patent No.: US 12,620,639 B2
(45) Date of Patent: May 5, 2026

(54) ADAPTER, TESTING APPARATUS, BATTERY CELL, BATTERY, AND ELECTRIC APPARATUS

(71) Applicant: CONTEMPORARY AMPEREX TECHNOLOGY CO., LIMITED, Ningde (CN)

(72) Inventors: Rongji Zhang, Ningde (CN); Bin Cao, Ningde (CN)

(73) Assignee: CONTEMPORARY AMPEREX TECHNOLOGY (HONG KONG) LIMITED, Hong Kong (CN)

( * ) Notice: Subject to any disclaimer, the term of this patent is extended or adjusted under 35 U.S.C. 154(b) by 404 days.

(21) Appl. No.: 18/352,956

(22) Filed: Jul. 14, 2023

(65) Prior Publication Data

US 2024/0021892 A1      Jan. 18, 2024

Related U.S. Application Data

(63) Continuation of application No. PCT/CN2023/082213, filed on Mar. 17, 2023.

(30) Foreign Application Priority Data

Apr. 2, 2022    (CN) .......................... 202220773221.2

(51) Int. Cl.
*H01M 10/42* (2006.01)
*G01N 33/00* (2006.01)
*H01M 50/636* (2021.01)

(52) U.S. Cl.
CPC .... *H01M 10/4285* (2013.01); *G01N 33/0027* (2013.01); *H01M 50/636* (2021.01)

(58) Field of Classification Search
CPC ........... H01M 10/4285; H01M 50/636; G01N 33/0027
See application file for complete search history.

(56) References Cited

U.S. PATENT DOCUMENTS

| | | | | |
|---|---|---|---|---|
| 3,661,009 | A | * | 5/1972 | Leonard ............. G01N 33/0013 73/31.03 |
| 2019/0113176 | A1 | | 4/2019 | Takizawa et al. |
| 2020/0141612 | A1 | | 5/2020 | Thibodeaux, Jr. |

FOREIGN PATENT DOCUMENTS

| | | |
|---|---|---|
| CN | 205228701 U | 5/2016 |
| CN | 109709282 A | 5/2019 |

(Continued)

OTHER PUBLICATIONS

The World Intellectual Property Organization (WIPO) International Search Report and Written Opinion for PCT/CN2023/082213 Jun. 21, 2023 13 Pages (including translation).

(Continued)

*Primary Examiner* — P. Macade Nichols
(74) *Attorney, Agent, or Firm* — ANOVA LAW GROUP, PLLC

(57) ABSTRACT

An adapter includes an adapting body and a valve body. The adapting body has a first mating portion and a second mating portion, where the first mating portion is configured to mate with an injection opening of a battery cell, the second mating portion is configured to mate with a gas detection apparatus, and a gas flow passage is constructed within an adapting body. The gas flow passage runs through the first mating portion and the second mating portion, and is configured for gas to flow from the injection opening to the gas detection apparatus.

20 Claims, 5 Drawing Sheets

(56)           References Cited

FOREIGN PATENT DOCUMENTS

| | | | |
|---|---|---|---|
| CN | 211955406 | U | 11/2020 |
| CN | 217507458 | U | 9/2022 |
| DE | 202008006949 | U1 | 9/2008 |
| GB | 205762 | A | 10/1923 |
| GB | 1127366 | A | 9/1968 |

OTHER PUBLICATIONS

State Intellectual Property Office of China Notice of Grant of Utility Model Patent Rights for Application No. 202220773221.2 Aug. 1, 2022 2 pages (including translation).

The European Patent Office (EPO) The Extended European Search Report for 23735579.7 May 8, 2024 6 Pages.

The European Patent Office (EPO) Communication pursuant to Article 94(3) EPC for Application No. 23735579.7 Feb. 5, 2025 5 Pages.

* cited by examiner

1000

100

30

313

312

311

313

310

316 a21 a2 a22 a a3 k(s)

a1

314a b

314a1

314b

315

317

ADAPTER, TESTING APPARATUS, BATTERY CELL, BATTERY, AND ELECTRIC APPARATUS

CROSS-REFERENCE TO RELATED APPLICATIONS

This application is a continuation of International Application No. PCT/CN2023/082213, filed on Mar. 17, 2023, which claims priority to Chinese Patent Application No. CN202220773221.2, filed on Apr. 2, 2022 and entitled "ADAPTER, TESTING APPARATUS, BATTERY CELL, BATTERY, AND ELECTRIC APPARATUS", which are incorporated herein by reference in their entirety.

TECHNICAL FIELD

This application relates to the field of battery testing technologies, and in particular, to an adapter, a testing apparatus, a battery cell, a battery, and an electric apparatus.

BACKGROUND

In related technologies, a solution for testing an internal pressure of a battery cell is to seal and weld an adapter at an injection opening of the battery cell, and use the adapter to connect the injection opening and a sensor. During testing, gas generated inside the battery cell is collected by the sensor through the adapter, and then a detection result is obtained through the sensor. In this technology, the battery cell needs to be installed with both the adapter and the sensor during transportation of the battery cell for testing, resulting in inconvenience in transporting the battery cell.

SUMMARY

In view of the above problems, this application provides an adapter, a testing apparatus, a battery cell, a battery, and an electric apparatus, so as to solve the problem that a battery cell needs to be installed with both an adapter and a sensor during transportation of the battery cell for testing, resulting in inconvenience in transporting the battery cell.

According to a first aspect, this application provides an adapter, including an adapting body and a valve body. The adapting body has a first mating portion and a second mating portion, where the first mating portion is configured to mate with an injection opening of a battery cell, the second mating portion is configured to mate with a gas detection apparatus, and a gas flow passage is constructed within the adapting body, the gas flow passage running through the first mating portion and the second mating portion and being configured for gas to flow from the injection opening to the gas detection apparatus. The valve body is constructed to be movably disposed on the adapting body and is movable relative to the adapting body when controlled to switch between states of turning on and off the gas flow passage.

In the technical solution in embodiments of this application, since the valve body of the adapter can be controlled to switch to the state of turning off the gas flow passage, only the adapter needs to be mounted on the battery cell during transportation of the battery cell for testing, and no gas detection apparatus needs to be connected to the adapter to ensure gas tightness of the battery cell for testing, so that it is more convenient to transport the battery cell.

In some embodiments, the gas flow passage includes a first passage, a second passage, and a mounting cavity, where the first passage runs through the first mating portion, the second passage runs through the second mating portion, and the mounting cavity connects the first passage and the second passage. The valve body is at least partially disposed in the mounting cavity and is constructed to be capable of switching between an off state and an on state when moving relative to the mounting cavity, where the valve body blocks the first passage and/or the second passage when in the off state, and the valve body is away from both the first passage and the second passage when in the on state. In this case, the gas flow passage is divided into three parts: the first passage, the second passage, and the mounting cavity. With the valve body at least partially disposed in the mounting cavity, the valve body is controlled to switch between the two states of turning on and off the gas flow passage by at least changing a position of the portion thereof located in the mounting cavity, making the structure simple and the control reliable.

In some embodiments, the first passage and the second passage run through two intersecting inner walls of the mounting cavity, respectively, and the valve body is constructed to be movable relative to the mounting cavity when controlled, with one of the two inner walls located in a moving direction of the valve body and the other spaced apart from the valve body. In this case, the first passage and the second passage run through the two intersecting inner walls of the mounting cavity, respectively, which means that the first passage and the second passage extend to intersect, so that the gas flow passage is not very long in all directions, thereby avoiding a large size of the adapter in one direction and making transportation more convenient. In addition, the valve body only needs to move to open or close the intersection on one of the inner walls to turn on or off the gas flow passage, making the structure simple and easy to control.

In some embodiments, the adapter further includes a first sealing member, where the first sealing member is disposed in the mounting cavity, and the first sealing member is capable of hermetically connecting the valve body and the inner wall in the moving direction of the valve body. In this case, the provision of the first sealing member can improve the gas tightness and prevent gas leakage from the adapter.

In some embodiments, the gas flow passage includes a mounting hole, where the mounting hole is formed in the second mating portion, and the mounting hole is configured to be sleeved around the gas detection apparatus. In this case, the mounting hole being formed in the second mating portion can not only allow for mating with a connection tube, but also facilitate the sampling of the gas detection apparatus, making the structure simple and the manufacturing costs low.

In some embodiments, the second mating portion is provided with an engaging member, where the engaging member has an engaging hole, the engaging hole is coaxially connected to the mounting hole, and the engaging hole is constructed to be capable of being engaged with and sleeved around a gas detection apparatus. In this case, when inserted into the engaging hole, the connection tube can be locked with the engaging member, so as to prevent the connection tube from falling off, fixedly mounting the connection tube and enhancing the reliability of the testing process.

In some embodiments, the engaging member is constructed to be capable of being extruded by the gas detection apparatus in the engaging hole to allow elastic deformation in the radial direction of the engaging hole to clamp the gas detection apparatus. In this case, the connection tube is fixedly mounted by utilizing an elastic restoring force generated by the engaging member during elastic deformation to tightly clamp the connection tube. As compared with other locking modes, this structure is simpler.

In some embodiments, the engaging member includes a clamp, where the clamp itself is enclosed to form the engaging hole, the clamp is hermetically connected to the mounting cavity, an axial end of the clamp extends into the mounting hole, and a first elastic arm is provided on the end portion of the axial end, the first elastic arm being capable of undergoing elastic deformation in the radial direction of the engaging hole. In this case, after inserted into the engaging hole for a period of time, the connection tube is clamped by the elastic restoring force generated by the first elastic arm, which facilitates the mounting of the connection tube. In addition, the first elastic arm is provided at the axial end, which is convenient for processing and manufacturing.

In some embodiments, the engaging member further includes an expansion sleeve, where the expansion sleeve is constructed to be capable of being movably sleeved in the engaging hole in the axial direction of the engaging hole, the expansion sleeve has a mating hole, the mating hole is coaxially disposed with the engaging hole, the mating hole is configured to mate with the gas detection apparatus, and the first elastic arm is squeezed at a position in the movement path of the expansion sleeve. In this case, when inserting and removing the connection tube, the first elastic arm is first propped open using the expansion sleeve, then the expansion sleeve is used to switch the elastic restoring force of the first elastic arm acting on the connection tube, and the connection tube is inserted and removed without the action of the elastic arm, so that fast insertion and removal of the connection tube can be achieved.

In some embodiments, the adapter further includes a second sealing member, where the second sealing member is disposed in the mounting hole, and the second sealing member is configured to be capable of hermetically connecting the gas detection apparatus and the gas flow passage. In this case, the tightness of the gas flow passage and the gas detection apparatus is achieved by using the second sealing member disposed in the mounting hole.

In some embodiments, the gas flow passage further includes an intermediate hole, where the intermediate hole is formed in the second mating portion and coaxially connected to the mounting hole, the mounting hole has an inner side wall, the intermediate hole runs through the inner side wall, and the second sealing member is disposed in the inner side wall and provided around the intermediate hole. In this case, the second sealing member is used to achieve tightness of the gas detection apparatus and the gas flow passage, and it is not necessary to maintain the tightness of the mounting hole and the gas detection apparatus, which facilitates insertion of the connection tube of the gas detection apparatus and makes the structure simpler.

In some embodiments, the first mating portion is removably connected to the injection opening. When there is no need to test the battery cell, the adapter can be removed to facilitate combination of battery cells with each other.

In some embodiments, the first mating portion is threadedly connected to the injection opening. In this way, it is not only easy to disassemble and assemble the first mating portion, but also can more conveniently ensure tightness.

In some embodiments, the adapter further includes a third sealing member, the third sealing member being configured to hermetically connect the first mating portion and the injection opening. In this case, the third sealing member may be used to ensure the gas tightness between the adapter and the injection opening.

According to a second aspect, this application provides a testing apparatus, including a gas detection apparatus and an adapter according to any of the foregoing embodiments, where the gas detection apparatus includes a connection tube and a detector that are connected, the connection tube is configured to mate with a second mating portion, the detector is configured to obtain characteristic information about gas flowing through the connection tube, and the characteristic information includes gas pressure information and/or gas composition information.

In some embodiments, grease is adhered to the wall of the connection tube. In this case, the grease occupies the space inside the connection tube, so that air pressure inside the connection tube can be closer to the original air pressure environment inside the battery cell, which can improve the detection accuracy.

According to a third aspect, this application provides a battery cell, which includes an adapter in the foregoing embodiments.

In some embodiments, the battery cell also includes a sealing nail, and a selected one of the first mating portion and the sealing nail is threadedly connected to the injection opening. When there is no need to test the battery cell, the sealing nail may be threadedly connected to the injection opening to seal the injection opening. When testing is required, the first mating portion of the adapter may be threadedly connected to the injection opening. Use of the threaded connection facilitates switching of the battery cell between testing and non-testing cases.

According to a fourth aspect, this application provides a battery, including the battery cell in the foregoing embodiments.

According to a fifth aspect, this application provides an electric apparatus, including the battery in the foregoing embodiments, where the battery is configured to supply electric energy.

The foregoing description is merely an overview of the technical solution of this application. For a better understanding of the technical means in this application such that they can be implemented according to the content of the specification, and to make the above and other objectives, features and advantages of this application more obvious and easier to understand, the following describes specific embodiments of this application.

BRIEF DESCRIPTION OF DRAWINGS

Persons of ordinary skill in the art can clearly understand various other advantages and benefits by reading the detailed description of the embodiments below. The accompanying drawings are merely intended to illustrate some embodiments and are not intended to limit this application. In addition, in all the accompanying drawings, same parts are indicated by same accompanying symbols. In the accompanying drawings.

Figure 1:
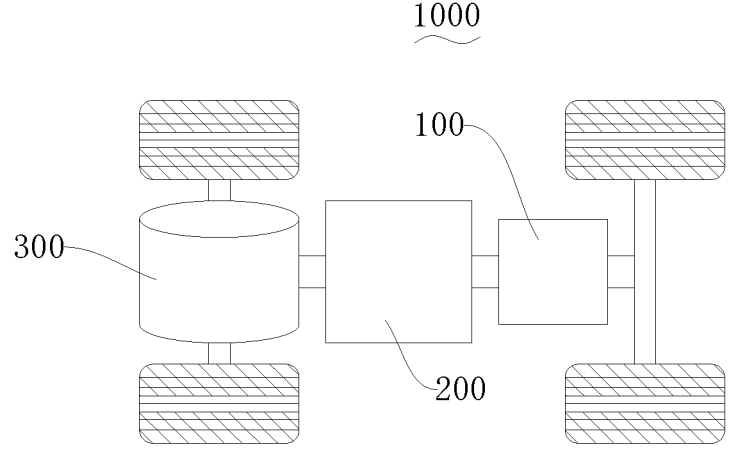
FIG. 1 is a schematic structural diagram of a vehicle according to some embodiments of this application.

Reference signs in specific embodiments are as follows: 1000. vehicle; 100. battery; 200. controller; 300. motor; 10. box; 11. first portion; 12. second portion; 20. battery cell; 21. end cover; 21*a*. electrode terminal; 22. housing; 23. cell assembly; 23*a*. tab; 26. sealing nail; 30. adapter; 310. adapting body; 311. first mating portion; 312. second mating portion; a. gas flow passage; a1. first passage; a2. second passage; a21. mounting hole; a22. intermediate hole; a3. mounting cavity; b. inner side wall; 313. valve body; 314. engaging member; 314*a*. clamp; k(s). engaging hole; 314*a*1. first elastic arm; 314*b*. expansion sleeve; k. mating hole; 315. first sealing member 316. second sealing member; 317. third sealing member; 40. gas detection apparatus; and 41. connection tube.

DESCRIPTION OF EMBODIMENTS

The following describes in detail the embodiments of technical solutions of this application with reference to the accompanying drawings. The following embodiments are merely intended for a clearer description of the technical solutions of this application and therefore are used as just examples which do not constitute any limitations on the protection scope of this application.

Unless otherwise defined, all technical and scientific terms used herein shall have the same meanings as commonly understood by those skilled in the art to which this application relates. The terms used herein are intended to merely describe the specific embodiments rather than to limit this application. The terms "include", "comprise", and "have" and any other variations thereof in the specification, claims and brief description of drawings of this application are intended to cover non-exclusive inclusions.

In the description of the embodiments of this application, the terms "first", "second", and the like, if any, are merely intended to distinguish between different objects, and shall not be understood as any indication or implication of relative importance or any implicit indication of the number, specific sequence, or primary-secondary relationship of the technical features indicated. In the description of this application, "a plurality of" means at least two unless otherwise specifically stated.

In this specification, reference to "embodiment" means that specific features, structures or characteristics described with reference to the embodiment may be incorporated in at least one embodiment of this application. The word "embodiment" appearing in various places in the specification does not necessarily refer to the same embodiment or an independent or alternative embodiment that is exclusive of other embodiments. It is explicitly or implicitly understood by persons skilled in the art that the embodiments described herein may be combined with other embodiments.

In the description of the embodiments of this application, the term "and/or", if any, is only an associative relationship for describing associated objects, indicating that three relationships may be present. For example, A and/or B may indicate the following three cases: presence of only A, presence of both A and B, and presence of only B. In addition, the character "/" in this specification generally indicates an "or" relationship between contextually associated objects.

In the description of the embodiments of this application, the term "a plurality of", if any, means more than two (inclusive). Similarly, "a plurality of groups" means more than two (inclusive) groups, and "a plurality of pieces" means more than two (inclusive) pieces.

In the description of the embodiments of this application, the orientations or positional relationships indicated by the technical terms "center", "longitudinal" "transverse", "length", "width", "thickness", "upper", "lower", "front", "rear", "left", "right", "perpendicular", "horizontal", "top", "bottom", "inside", "outside", "clockwise", "counterclockwise", "axial", "radial", "circumferential", and the like, if any, are based on the orientations or positional relationships as shown in the accompanying drawings. These terms are merely for ease and brevity of the description of the embodiments of this application rather than indicating or implying that the apparatuses or components mentioned must have specific orientations, or must be constructed or manipulated according to specific orientations, and therefore shall not be construed as any limitations on the embodiments of this application.

In the description of the embodiments of this application, unless otherwise specified and defined explicitly, the terms "mount", "connect", "join", and "fasten", if any, should be understood in their general senses. For example, they may refer to a fixed connection, a detachable connection, or an integral connection, may refer to a mechanical connection or electrical connection, and may refer to a direct connection, an indirect connection via an intermediate medium, or an internal communication or an interaction between two elements. Persons of ordinary skill in the art can understand specific meanings of these terms in this application as appropriate to specific situations.

In the related art, when an internal pressure test is performed on a battery cell, during transportation of the battery cell for testing, both an adapter and a sensing apparatus need to be mounted on the battery cell, resulting in inconvenient transportation of the battery cell. A main reason is that the battery cell with the adapter mounted is in communication with the outside, and the mounting of the sensing apparatus on the adapter can keep the inside of the battery cell always connected to the sensing apparatus and isolated from the outside, that is, using the sensing apparatus to ensure the gas tightness of the battery cell during transportation.

To solve the problem of inconvenient transportation of the battery cell, mounting of the sensor apparatus can be omitted when the adapter is used to ensure the gas tightness of the battery cell during transportation, allowing more convenient transportation of the battery cell. Specifically, the gas flow passage inside the adapter is designed to be switchable in the on state, and the gas flow passage of the adapter is switched to the off state when only the adapter is mounted during transportation, to ensure the gas tightness during transportation.

Based on the above considerations, in order to solve the problem of inconvenient transportation of battery cell, the inventors of this application, after in-depth research, have designed an adapter. A valve body is disposed on the adapter, and the valve body can change an on state of a gas flow passage inside the adapter, so that during transportation, the gas flow passage is turned off to ensure the gas tightness, facilitating transportation of the battery cell.

The battery cell disclosed in the embodiments of this application may be used without limitation in an electric apparatus such as a vehicle, a ship, or an aircraft. The battery cell, battery, and the like disclosed in this application may be used to constitute a power supply system of that electric apparatus.

An embodiment of this application provides an electric apparatus that uses a battery as a power source. The electric apparatus may be but is not limited to a mobile phone, a tablet, a laptop computer, an electric toy, an electric tool, an electric bicycle, an electric car, a ship, or a spacecraft. The electric toy may be a fixed or mobile electric toy, for example, a game console, an electric toy car, an electric toy ship, and an electric toy airplane. The spacecraft may include an airplane, a rocket, a space shuttle, a spaceship, and the like.

For ease of description, the electric apparatus of an embodiment of the application being a vehicle 1000 is used as an example for description of the following embodiments.

Referring to FIG. 1, FIG. 1 is a schematic structural diagram of a vehicle 1000 according to some embodiments of this application. The vehicle 1000 may be a fossil fuel vehicle, a natural-gas vehicle, or a new energy vehicle, where the new energy vehicle may be a battery electric vehicle, a hybrid electric vehicle, a range-extended vehicle, or the like. The vehicle 1000 is provided with a battery 100 inside, and the battery 100 may be disposed at the bottom, front, or rear of the vehicle 1000. The battery 100 may be configured to supply power to the vehicle 1000. For example, the battery 100 may be used as an operational power supply for the vehicle 1000. The vehicle 1000 may further include a controller 200 and a motor 300, where the controller 200 is configured to control the battery 100 to supply power to the motor 300, for example, to satisfy a working electricity need during start, navigation, and driving of the vehicle 1000.

In some embodiments of this application, the battery 100 can be used as not only the operational power source for the vehicle 1000 but also a driving power source for the vehicle 1000, replacing or partially replacing fossil fuel or natural gas to provide driving traction for the vehicle 1000.

Figure 2:
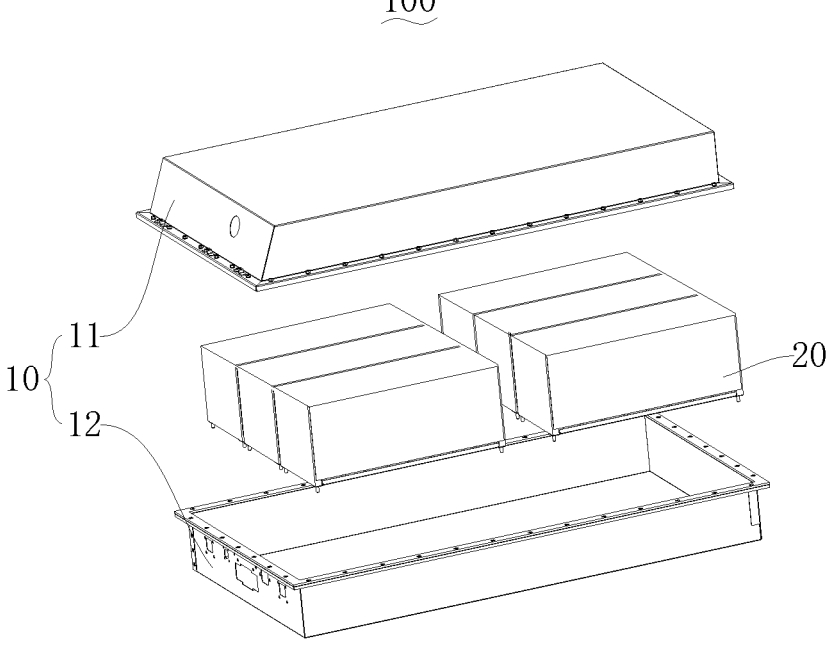
FIG. 2 is a schematic structural exploded view of a battery according to some embodiments of this application.

Referring to FIG. 2, FIG. 2 is an exploded view of a battery 100 according to some embodiments of this application. The battery 100 includes a box 10 and a battery cell 20, where the battery cell 20 is accommodated in the box 10. The box 10 is configured to provide an accommodating space for the battery cell 20. The box 10 may be a variety of structures. In some embodiments, the box 10 may include a first portion 11 and a second portion 12. The first portion 11 and the second portion 12 fit together to jointly define a space for accommodating the battery cell 20. The second portion 12 may be a hollow structure with an opening at one end, and the first portion 11 may be a plate-shaped structure, where the first portion 11 covers the opening side of the second portion 12 for the first portion 11 and the second portion 12 to jointly define an accommodating space. Alternatively, both the first portion 11 and the second portion 12 may be hollow structures with an opening at one side, and the opening side of the first portion 11 is engaged with the opening side of the second portion 12. Certainly, the box 10 formed by the first portion 11 and the second portion 12 may have a variety of shapes, for example, cylinder or cuboid.

In the battery 100, the battery cell 20 may be present in plurality, and the plurality of battery cells 20 may be connected in series, parallel, or series-parallel, where being connected in series-parallel means a combination of series and parallel connections of the plurality of battery cells 20. The plurality of battery cells 20 may be directly connected in series, parallel, or series-parallel, and then an entirety of the plurality of battery cells 20 is accommodated in the box 10; or certainly, the battery 100 may be formed by a plurality of battery cells 20 connected in series, parallel, or series-parallel first to form a battery module and then a plurality of battery modules being connected in series, parallel, or series-parallel to form an entirety which is accommodated in the box 10. The battery 100 may further include other structures. For example, the battery 100 may further include a busbar configured to implement electrical connection between the plurality of battery cells 20.

Each battery cell 20 may be a secondary battery or a primary battery, and may be a lithium-sulfur battery, a sodium-ion battery, or a magnesium-ion battery, without being limited thereto. The battery cell 20 may be cylindrical, flat, cuboid, or of other shapes.

Figure 3:
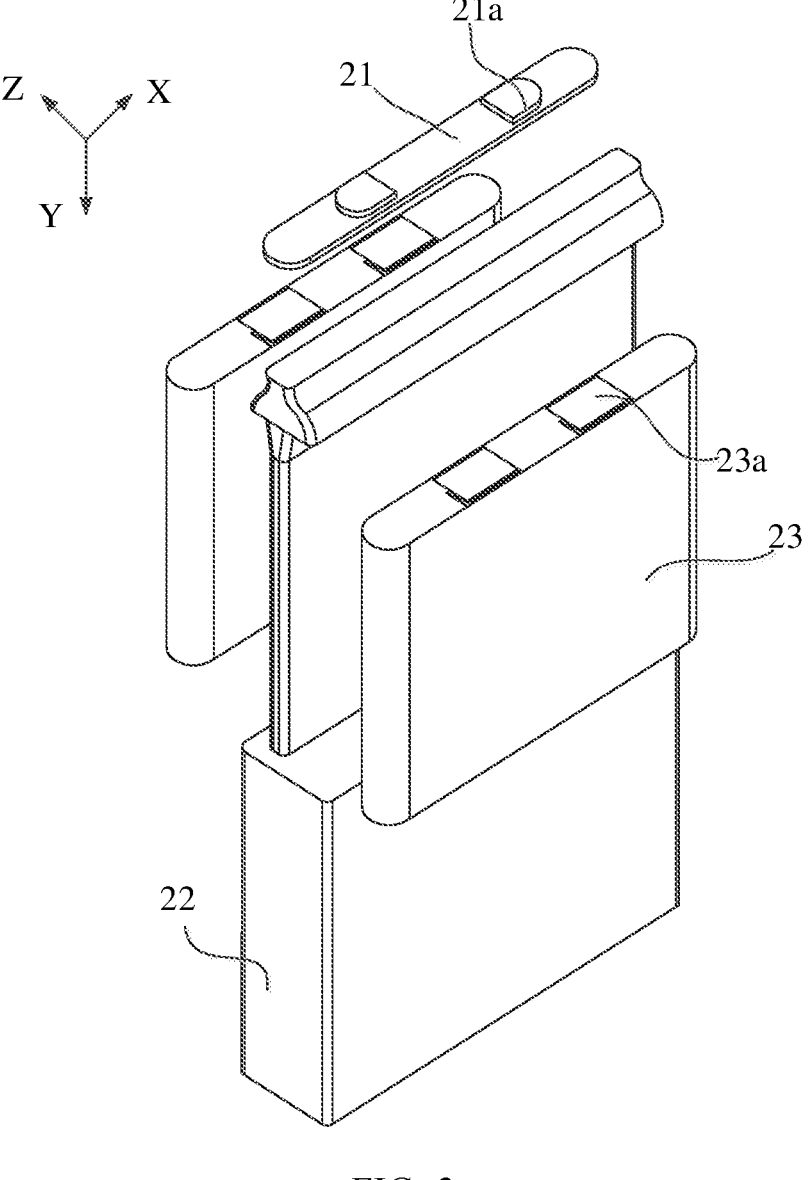
FIG. 3 is a schematic structural exploded view of a battery cell according to some embodiments of this application.
Figure 4:
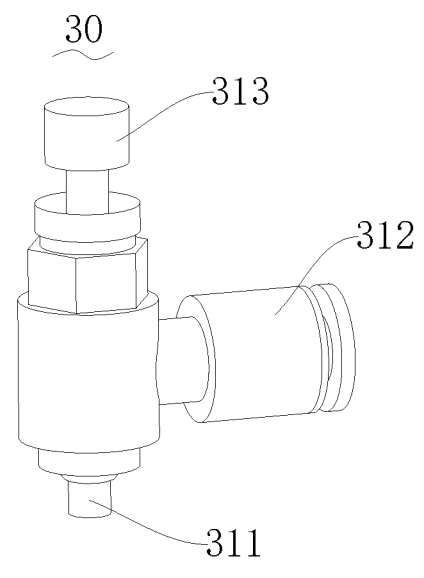
FIG. 4 is a schematic structural diagram of an adapter according to an embodiment of this application.

Referring to FIG. 3, FIG. 3 is a schematic structural exploded view of a battery cell 20 according to some embodiments of this application. The battery cell 20 refers to a smallest unit constituting a battery. As shown in FIG. 3, the battery cell 20 includes an end cover 21, a housing 22, a cell assembly 23, and other functional components.

The end cover 21 refers to a component that covers an opening of the housing 22 to isolate an internal environment of the battery cell 20 from an external environment. A shape of the end cover 21 is not limited and may be adapted to a shape of the housing 22 to fit the housing 22. Optionally, the end cover 21 may be made of a material with specified hardness and strength (for example, aluminum alloy), so that the end cover 21 is less likely to deform when subjected to extrusion and collision, allowing the battery cell 20 to have higher structural strength and enhanced safety performance. Functional components such as an electrode terminal 21a may be provided on the end cover 21. The electrode terminal 21a may be configured to electrically connect to the cell assembly 23 for outputting or inputting electric energy of the battery cell 20. In some embodiments, the end cover 21 may further be provided with a pressure relief mechanism for releasing internal pressure when the internal pressure or a temperature of the battery cell 20 reaches a threshold. The end cover 21 may also be made of various materials, such as copper, iron, aluminum, stainless steel, aluminum alloy, and plastic, which are not particularly limited in the embodiments of this application. In some embodiments, an insulator may also be provided at an inner side of the end cover 21. The insulator may be configured to isolate an electrically connected component in the housing 22 from the end cover 21 to reduce a risk of short circuit. For example, the insulator may be made of plastic, rubber, or the like.

The housing 22 is an assembly configured to form the internal environment of the battery cell 20 together with the end cover 21, where the formed internal environment may be configured to accommodate the cell assembly 23, an electrolyte, and other components. The housing 22 and the end cover 21 may be separate components, an opening may be provided on the housing 22, and the end cover 21 covers the opening to form the internal environment of the battery cell 20. The end cover 21 and the housing 22 are not limited and may also be integrated. Specifically, the end cover 21 and the housing 22 may form a shared connection surface before other components are disposed inside the housing, and then the housing 22 is covered with the end cover 21 when inside of the housing 22 needs to be enclosed. The housing 22 may be of various shapes and sizes, such as a cuboid shape, a cylindrical shape, and a hexagonal prism shape. Specifically, a shape of the housing 22 may be determined according to a specific shape and size of the cell assembly 23. The housing 22 may be made of various materials, such as copper, iron, aluminum, stainless steel, aluminum alloy, and plastic, which are not particularly limited in the embodiments of this application.

The cell assembly 23 is a component in the battery cell 100 in which electrochemical reactions occur. The housing 22 may include one or more cell assemblies 23. The cell assembly 23 is mainly formed by winding or stacking a positive electrode plate and a negative electrode plate, and a separator is generally provided between the positive electrode plate and the negative electrode plate. Parts of the positive electrode plate and the negative electrode plate with active substances constitute a body portion of the cell assembly, while parts of the positive electrode plate and the negative electrode plate without active substances separately constitute a tab 23a. A positive electrode tab and a negative electrode tab may both be located at one end of the body portion or be located at two ends of the body portion respectively. During charge and discharge of the battery, a positive electrode active substance and a negative electrode active substance react with an electrolyte, and the tabs 23a are connected to the electrode terminals to form a current loop.

The following is a detailed description of an adapter provided in the embodiments of this application.

According to some embodiments of this application, referring to FIG. 4, FIG. 5, FIG. 6, and FIG. 7, an adapter 30 according to an aspect of this application includes an adapting body 310 and a valve body 313. The adapting body 310 has a first mating portion 311 and a second mating portion 312, where the first mating portion 311 is configured to mate with an injection opening of the battery cell 20, the second mating portion 312 is configured to mate with a gas detection apparatus 40, and a gas flow passage a is constructed within the adapting body 310, the gas flow passage a running through the first mating portion 311 and the second mating portion 312 and being configured for gas to flow from the injection opening to the gas detection apparatus 40. The valve body 313 is constructed to be movably disposed on the adapting body 310 and is movable relative to the adapting body 310 when controlled to switch between states of turning on and off the gas flow passage a.

The valve body 313 is movably disposed on the adapting body 310, which means that the valve body 313 is movable relative to the adapting body 310, including the valve body 313 rotating relative to the adapting body 310, the valve body 313 moving relative to the adapting body 310, or the valve body 313 deforming relative to the adapting body 310. A specific manner in which the valve body 313 switches between on and off states of the gas flow passage a while the adapting body 310 undergoes deformation may be as follows: The valve body 313 has a deformation portion located within the gas flow passage a, and the deformation portion may switch between the states of turning on and off the gas flow passage a when controlled to expand or contract (for example, an airbag); or the deformation portion may switch between the states of turning on and off the gas flow passage a when stretched or shortened (for example, a telescopic plate).

Specific forms of the first mating portion 311 and the second mating portion 312 depend on a form of mating between the injection opening and the gas detection apparatus 40. This is not limited herein. For example, the first mating portion 311 is welded to the injection opening, and the second mating portion 312 is removably mated to the gas detection apparatus 40. For another example, the first mating portion 311 is removably and threadedly connected to the injection opening, and the second mating portion 312 is removably locked with the gas detection apparatus 40. It should be noted that the first mating portion 311 is hermetically mated to the injection opening of the battery cell 20, and the second mating portion 312 is hermetically mated to the gas detection apparatus 40.

The gas detection apparatus 40 depends on an actual requirement. For example, when pressure inside the battery cell 20 needs to be detected, the gas detection apparatus 40 may be an apparatus capable of detecting the gas pressure. For another example, when compositions of gas generated inside the battery cell 20 are to be detected, the gas detection apparatus 40 may be an apparatus capable of detecting the gas composition. A specific type of gas detection apparatus 40 is not limited in this application. In other words, application of the adapter 30 in this application is not limited to a scenario in which the internal pressure test is performed on the battery cell 20.

The first mating portion 311 of the adapter 30 is hermetically mounted at the injection opening of the battery cell 20 before testing, and the gas flow passage a is connected to the inside of the battery cell 20 through the injection opening. When the valve body 313 of the adapter 30 is controlled to be in the state of turning off the gas flow passage a relative to the adapting body 310, and the gas and other substances inside the battery cell 20 cannot leak out through the gas flow passage a, so that the gas tightness inside the battery cell 20 can be maintained, and no gas leakage occurs during transportation of the battery cell 20. In testing, the second mating portion 312 is mated to the gas detection apparatus 40, and the valve body 313 of the adapter 30 is controlled to be in the state of turning on the gas flow passage a relative to the adapting body 310, so that the gas and other substances generated inside the battery cell 20 during testing can go through the injection opening and the gas flow passage a and eventually enter the gas detection apparatus 40, and test results are finally obtained through the gas detection apparatus 40.

Compared with the related art, since the valve body 313 of the adapter 30 can be controlled to switch to the state of turning off the gas flow passage a, only the adapter 30 is needed on the battery cell 20 during transportation of the battery cell 20 for testing, and no gas detection apparatus 40 needs to be connected to ensure the gas tightness of the battery cell 20 for testing, so that it is more convenient to transport the battery cell 20.

Figure 5:
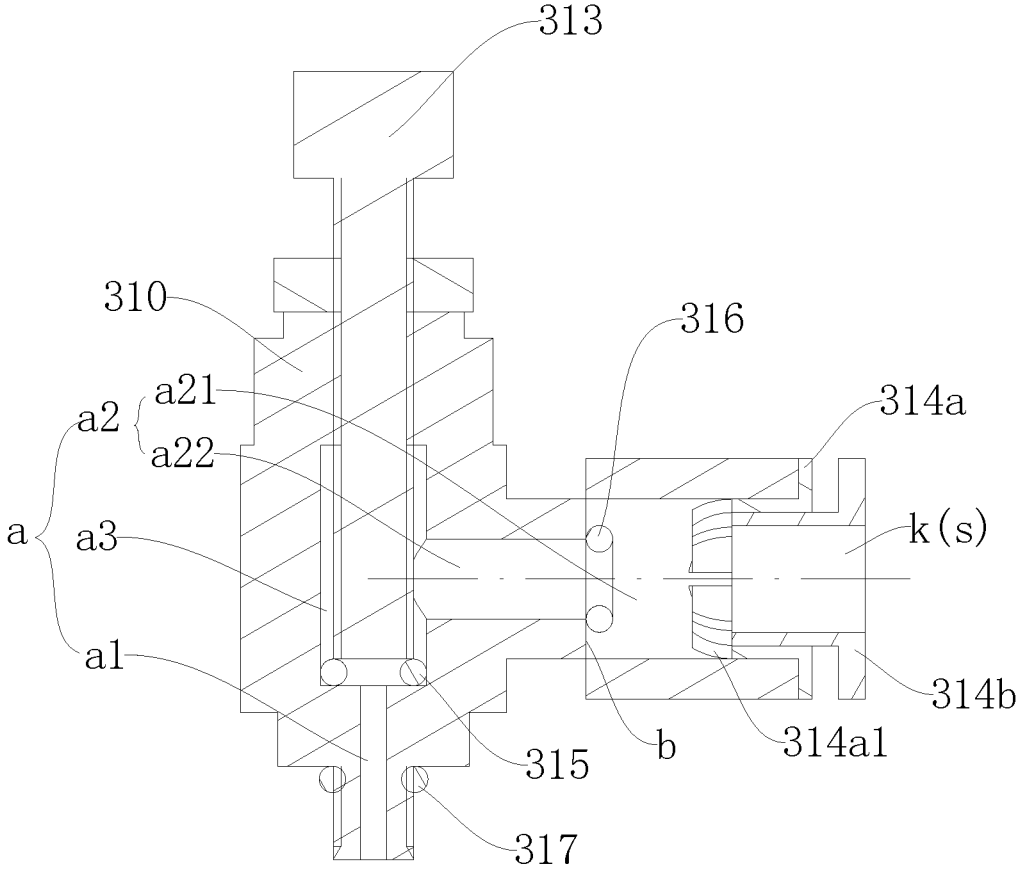
FIG. 5 is a cross-sectional view of the adapter shown in FIG. 4.

In some embodiments of this application, referring to FIG. 5, the gas flow passage a includes a first passage a1, a second passage a2, and a mounting cavity a3. The first passage a1 runs through the first mating portion 311, the second passage a2 runs through the second mating portion 312, and the mounting cavity a3 connects the first passage a1 and the second passage a2. The valve body 313 is at least partially disposed in the mounting cavity a3 and is constructed to be capable of switching between an off state and an on state when controlled to move relative to the mounting cavity a3. When in the off state, the valve body 313 blocks the first passage a1 and/or the second passage a2, and when in the on state, the valve body 313 is away from both the first passage a1 and the second passage a2.

The valve body 313 may be fully or partially located in the mounting cavity a3, as long as the valve body 313 can move relative to the mounting cavity a3. For example, the valve body 313 includes a driving part and a blocking part, and the driving part may be controlled to drive the blocking part to rotate relative to the mounting cavity a3. In this case, both the driving part and the blocking part are located in the mounting cavity a3. A driving button is provided on the adapter 30, and the driving button is electrically connected to the driving part. When a user operates the driving button to control the action of the driving part, the driving part (for example, a motor) can drive the blocking part to act and switch between the off state of blocking the first passage a1 and/or the second passage a2 and the on state of being away from the first passage a1 and the second passage a2. In this case, it is also possible that the blocking part is located inside the mounting cavity a3, and the driving part is partially located outside the adapting body 310 for user operation. When the user operates the driving part (for example, a driving handle), the driving part drives the blocking part to act and switch between the off state and the on state.

It can be understood that when the valve body 313 blocks the first passage a1 and/or the second passage a2, the gas cannot flow smoothly in the gas flow passage a, and in this case, the valve body 313 turns off the gas flow passage. When the valve body 313 is away from the first passage a1 and the second passage a2, the gas can flow smoothly in the gas flow passage a, and in this case, the valve body 313 turns on the gas flow passage a.

In this embodiment, the gas flow passage a is divided into three parts: the first passage a1, the second passage a2, and the mounting cavity a3. with the valve body 313 at least partially disposed in the mounting cavity a3, the valve body 313 is controlled to switch between the two states of turning on and off the gas flow passage a by at least changing a position of the portion thereof located in the mounting cavity a3, making the structure simple and the control reliable.

In some embodiments of this application, still referring to FIG. 5, the first passage a1 and the second passage a2 run through two intersecting inner walls of the mounting cavity a3, respectively, and the valve body 313 is constructed to be movable relative to the mounting cavity a3 when controlled, with one of the two inner walls located in a moving direction of the valve body 313 and the other spaced apart from the valve body 313.

One of the two inner walls being in a moving direction of the valve body 313 is defined as a first inner wall, and the other inner wall is defined as a second inner wall, where the first passage a1 (or the second passage a2) runs through the first inner wall to form a first intersection, and the second passage a2 (or the first passage a1) runs through the second inner wall to form a second intersection. The moving valve body 313 may open or close the first intersection, and the valve body 313 is always spaced apart from the second intersection. Therefore, when the valve body 313 closes the first intersection, the gas flow passage a is turned off, and when the valve body 313 opens the first intersection, the gas flow passage a is turned on.

In this case, the first passage a1 and the second passage a2 run through the two intersecting inner walls of the mounting cavity a3, respectively, which means that the first passage a1 and the second passage a2 extend to intersect, so that the gas flow passage a is not very long in all directions, thereby avoiding a large size of the adapter 30 in one direction and making transportation of the battery cell more convenient. In addition, the valve body 313 only needs to move to open or close the intersection on one of the inner walls to turn on or off of the gas flow passage a, making the structure simple and easy to control.

It can be understood that in other embodiments, the valve body 313 in moving may turn on or off the gas flow passage a in a way, including but not limited to: The valve body 313 in moving does not come into contact with the inner wall in its moving direction, but blocks or opens the intersection on the other inner wall through a side wall parallel to its moving direction, so as to turn on or off the gas flow passage a. In other embodiments, the valve body 313 may alternatively open or close the intersection on one of the inner walls during rotation to turn on or off the gas flow passage a.

In some embodiments of this application, still referring to FIG. 5, the adapter 30 further includes a first sealing member 315 disposed in the mounting cavity a3, the first sealing member 315 being capable of hermetically connecting the valve body 313 and the inner wall in the moving direction of the valve body 313.

It can be understood that when the valve body 313 comes into contact the first inner wall in its moving direction, the first sealing member 315 can hermetically connect the valve body 313 to the first inner wall, thus achieving a hermetic connection between the valve body 313 and the first inner wall, so that the gas flowing out of the passage running through the first inner wall does not leak into the mounting cavity a3. Specifically, the first sealing member 315 may be fixed on an end of the valve body 313 facing the inner wall to which the valve body 313 is hermetically connected, and the first sealing member 315 may alternatively be fixed at the intersection on the inner wall in the moving direction of the valve body 313. This is not limited herein.

The first sealing member 315 may be a sealing ring, a sealing gasket, or the like.

The provision of the first sealing member 315 in this embodiment can improve the gas tightness and prevent gas leakage from the adapter 30.

Certainly, in other embodiments, with the valve body 313 itself in hermetic contact with the first inner wall, a hermetic connection between the valve body 313 and the first inner wall may be achieved. For example, the valve body 313 is made of a sealing material.

Figure 8:
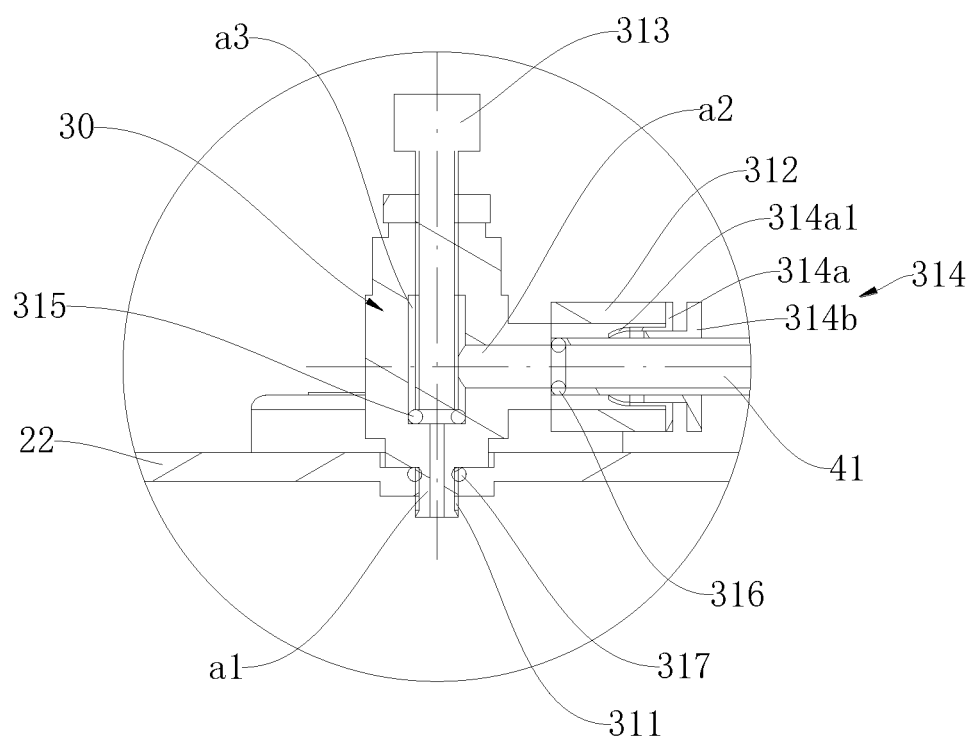
FIG. 8 is an enlarged view of position A in FIG. 7.

In some embodiments of this application, still referring to FIG. 5 and FIG. 8, the gas flow passage a includes a mounting hole a21. The mounting hole a21 is formed in the second mating portion 312, and the mounting hole a21 is configured to be sleeved around the gas detection apparatus 40.

The gas detection apparatus 40 generally has a connection tube 41. During assembly of the adapter 30 and the gas detection apparatus, a connection tube is sleeved into the mounting hole a21, and the gas inside the battery cell 20 can enter into the connection tube 41 through the mounting hole a21, and then enter into the gas detection apparatus 40 for analysis and detection. The connection tube 41 of the gas detection apparatus 40 may be a rigid tube, a flexible tube, a tube-type interface, or the like, and is not limited in its specific form as long as it can be connected to the interior of the gas detection apparatus 40 and the gas flow passage a.

In this case, the mounting hole a21 being formed in the second mating portion 312 can not only allow for mating with a connection tube 41, but also facilitate sampling of the gas detection apparatus 40, making the structure simple and the manufacturing costs low.

The mounting hole a21 may be directly sealed with the connection tube 41 of the gas detection apparatus 40 to ensure fixed mounting of the connection tube 41 on the second mating portion 312, or the solutions in following embodiments can be used to achieve the fixed mounting of the connection tube 41.

In some embodiments of this application, still referring to FIG. 5 and FIG. 8, the second mating portion 312 is provided with an engaging member 314, where the engaging member 314 has an engaging hole k(s), the engaging hole k(s) is coaxially connected to the mounting hole a21, and the engaging hole k(s) is constructed to be capable of being engaged with and sleeved around a gas detection apparatus.

During assembly of the adapter 30 and the gas detection apparatus, the connection tube 41 is inserted into the engaging hole k(s) of the engaging member 314 so that the connection tube 41 is sleeved in the mounting hole a21. When inserted into the engaging hole k(s), the connection tube 41 can be locked with the engaging member 314, so as to prevent the connection tube 41 from falling off, fixedly mounting the connection tube 41 and enhancing the reliability of the testing process.

The engaging member 314 is a member that can be locked with the connection tube 41 to achieve fixed mounting of the connection tube 41. The engaging member 314 can be locked with the connection tube 41 in various manners. For example, the engaging member 314 has an engaging sleeve and a threaded member, the engaging sleeve has an engaging hole, and the threaded member is threadedly sleeved around the outer wall of the engaging sleeve. When the connection tube 41 is inserted into the engaging hole k(s), rotation of the threaded member can allow the threaded member to apply tightening force to the connection tube 41 so as to prevent the connection tube 41 from falling off. The manner in which the engaging member 314 is locked with the connection tube 41 is not limited herein, as long as the connection tube 41 can be prevented from falling off. Certainly, it is also possible to adopt the solutions in following embodiments.

In some embodiments of this application, the engaging member 314 is constructed to be capable of being extruded by the gas detection apparatus 40 in the engaging hole k(s) to allow elastic deformation in the radial direction of the engaging hole k(s) to clamp the gas detection apparatus 40.

During assembly of the adapter 30 and the gas detection apparatus 40, when being inserted into the engaging hole k(s), the connection tube 41 of the gas detection apparatus 40 extrudes the engaging member 314. The engaging member 314 is elastically deformed in the radial direction under the extrusion of the connection tube 41 and the diameter of the engaging hole k(s) is enlarged to allow the insertion of the connection tube 41. An elastic restoring force is applied to the connection tube 41 when the elastic deformation of the engaging member 314 occurs, and the connection tube 41 (that is, the gas detection apparatus 40) is clamped tightly under the action of the elastic restoring force.

In withdrawing the connection tube 41 from the engaging member 314, because the extrusion of the connection tube 41 on the engaging member 314 gradually disappears, the elastic restoring force acting on the engaging member 314 gradually disappears, and the connection tube 41 withdraws more easily.

In this case, the elastic restoring force generated by the engaging member 314 during elastic deformation is used to tightly clamp the connection tube 41 to achieve a fixed mounting of the connection tube 41, making a structure simpler as compared with other locking modes.

There are various solutions to achieve the elastic deformation of the engaging member 314 in the radial direction under the extrusion of the connection tube 41 entering the engaging hole k(s). This is not limited herein. In an example, the engaging member 314 includes an engaging sleeve forming an engaging hole k(s) and an annular elastic sheet disposed around the engaging sleeve and axially disposed on the inner wall of the engaging sleeve. When being inserted into the engaging hole k(s), the connection tube 41 extends into and extrudes the annular elastic sheet, and then the annular elastic sheet reacts with an elastic restoring force to tightly clamp the connection tube 41. Certainly, it is also possible to adopt the solutions in following embodiments.

In some embodiments, still referring to FIG. 5 and FIG. 8, the engaging member 314 includes a clamp 314a, where the clamp 314a itself is enclosed to form the engaging hole k(s), the clamp 314a is hermetically connected to the second mating portion 312, an axial end of the clamp 314a extends into the mounting hole a21, and a first elastic arm 314a1 is provided on the end portion of the axial end, the first elastic arm 314a1 being capable of undergoing elastic deformation in the radial direction of the engaging hole k(s).

The first elastic arm 314a1 may be a ring-shaped elastic arm or a claw-shaped elastic arm. Specifically, the first elastic arm 314a1 may be formed by an elastic sheet, or the first elastic arm 314a1 may be formed by elastic rubber. This is not limited herein.

The other axial end of the clamp 314a may extend out of the mounting hole a21 or be located in the mounting hole a21, as long as the clamp 314a can be hermetically connected to the second mating portion 312.

When being inserted into the engaging hole k(s) to the axial end of the clamp 314a, the connection tube 41 of the gas detection apparatus 40 extrudes the first elastic arm 314a1. The first elastic arm 314a1 is elastically deformed in the radial direction under the extrusion of the connection tube 41 and enlarges the diameter of a portion of the engaging hole k(s) formed by itself to allow the insertion of the connection tube 41. The first elastic arm 314a1 in elastic deformation reacts with an elastic restoring force to the connection tube 41, to tightly clamp the connection tube 41 under the action of the elastic restoring force.

In this case, when being inserted into the clamp 314a, in the early stage, the connection tube 41 does not extrude the engaging hole k(s) and is not subject to the action of the elastic restoring force until the connection tube 41 is inserted into the axial end of the clamp 314a and is tightly clamped by the first elastic arm 314a1. In other words, the connection tube 41 is tightly clamped by the elastic restoring force generated by the first elastic arm 314a1 after the connection tube 41 has been inserted into the engaging hole k(s) for a period of time, facilitating mounting of the connection tube 41. In addition, the first elastic arm 314a1 is provided at the axial end, which is convenient for processing and manufacturing.

In other embodiments, the first elastic arm 314a1 may alternatively be provided on the other axial end of the clamp 314a that is located outside of the mounting hole a21 or faces outward.

In some embodiments, still referring to FIG. 5 and FIG. 8, the engaging member 314 further includes an expansion sleeve 314b, where the expansion sleeve 314b is constructed to be capable of being movably sleeved in the engaging hole k(s) in the axial direction of the engaging hole k(s), the expansion sleeve 314b has a mating hole k, the mating hole k is coaxially disposed with the engaging hole k(s), the mating hole k is configured to mate with the gas detection apparatus 40, and the first elastic arm 314a1 is squeezed at a position in a movement path of the expansion sleeve 314b.

The expansion sleeve 314b is a sleeve member with a certain strength and hardness, which may be a ceramic sleeve, a hard plastic sleeve, a metal sleeve, or the like. When pushing down the first elastic arm 314a1, the expansion sleeve 314b can cut off the elastic restoring force of the first elastic arm 314a1 acting on the connection tube 41.

In mounting the gas detection apparatus 40, the expansion sleeve 314b is first pushed axially forward to move to a position where the first elastic arm 314a1 is squeezed so as to make the engaging hole k(s) open wider at the first elastic arm 314a1, then the connection tube 41 is inserted into the mating hole k until the connection tube 41 is in place, and the connection tube 41 is not subject to the elastic restoring force of the first elastic arm 314a1 in the process. Later, the expansion sleeve 314b is pulled axially backward to make the expansion sleeve 314b withdraw from the first elastic arm 314a1 and the connection tube 41 remains in place, so that the first elastic arm 314a1 directly clamps the connection tube 41. Conversely, in pulling out the connection tube 41, the expansion sleeve 314b is first pressed to push the first elastic arm 314a1 down to release the first elastic arm 314a1 from clamping the connection tube 41, and then the connection tube 41 is pulled out.

In this way, when inserting and removing the connection tube 41, the first elastic arm 314a1 is first propped open using the expansion sleeve 314b, then the expansion sleeve 314b is used to switch the elastic restoring force of the first elastic arm 314a1 acting on the connection tube 41, and the connection tube 41 is inserted and removed without the action of the elastic arm 314a1, so that fast insertion and removal of the connection tube 41 can be achieved.

It should be noted that in the foregoing embodiments, the mounting hole a21 may be hermetically connected to the gas detection apparatus 40 or not. The mounting hole a21 is mainly used to mount the connection tube 41 of the gas detection apparatus 40. The tightness of the connection tube 41 and the gas flow passage a can be achieved by the mounting hole a21 or by other structures.

In some embodiments of this application, still referring to FIG. 5 and FIG. 8, the adapter 30 further includes a second sealing member 316, where the second sealing member 316 is disposed in the mounting hole a21, and the second sealing member 316 is configured to be capable of hermetically connecting the gas detection apparatus 40 and the gas flow passage a. In this case, the tightness of the gas flow passage a and the gas detection apparatus 40 is achieved by using the second sealing member 316 disposed in the mounting hole a21.

The second sealing member 316 may be a sealing ring, a sealing gasket, or the like. This is not limited herein. It can be understood that the second sealing member 316 is a sealing ring with an inner ring bore for fluid to pass through.

To enable the second sealing member 316 to hermetically connect the gas detection apparatus 40 and the gas flow passage a, in an optional embodiment, the second sealing member 316 is hermetically connected between the circumferential side wall of the mounting hole a21 and the connection tube 41. The second sealing member 316 may alternatively be provided by using the following solutions.

Specifically, in an embodiment, still referring to FIG. 5 and FIG. 8, the gas flow passage a further includes an intermediate hole a22, where the intermediate hole a22 is formed in the second mating portion 312, the intermediate hole a22 is coaxially connected to the mounting hole a21, the mounting hole a21 has an inner side wall b, the intermediate hole a22 runs through the inner side wall b, and the second sealing member 316 is disposed on the inner side wall b and provided around the intermediate hole a22.

In inserting the connection tube 41 of the gas detection apparatus 40 into the mounting hole a21, the axial end of the portion of the connection tube 41 that is inserted into the mounting hole a21 may abut against the second sealing member 316 and be connected to the intermediate hole a22, and the fluid flowing from the intermediate hole a22 may enter the connection tube 41 of the gas detection apparatus 40 directly through the intermediate hole a22 without leaking into the mounting hole a21.

In this case, the second sealing member 316 is used to achieve tightness of the gas detection apparatus 40 and the gas flow passage a, and it is not necessary to maintain the tightness of the mounting hole a21 and the gas detection apparatus 40, which facilitates insertion of the connection tube 41 of the gas detection apparatus 40 and makes the structure simpler.

In some embodiments of this application, the first mating portion 311 is removably connected to the injection opening. When the battery cell 20 is not needed for testing, the adapter 30 can be removed to facilitate combination of battery cells 20 with each other.

In an embodiment, the first mating portion 311 is threadedly connected to the injection opening. In this way, it is not only easy to disassemble and assemble the first mating portion, but also can more conveniently ensure the tightness. It is possible that the first mating portion 311 has external threads and that the injection opening has internal threads. Alternatively, the injection opening is provided with external threads, and the first mating portion 311 is provided with internal threads, as long as the two can be threadedly connected together. This is not limited herein.

In other embodiments, the first mating portion 311 and the injection opening may alternatively be removably connected in other manners, such as by engaging.

In some embodiments, still referring to FIG. 5 and FIG. 8, the adapter 30 further includes a third sealing member 317, the third sealing member 317 being configured to hermetically connect the first mating portion 311 and the injection opening. In this case, the third sealing member 317 may be used to ensure the gas tightness between the adapter 30 and the injection opening.

The third sealing member 317 may be a sealing ring or a sealing gasket. This is not limited herein.

Specifically, the third sealing member 317 is sleeved on external threads of the first mating portion 311. When the threaded connection between the injection opening and the first mating portion 311 is in place, the third sealing member 317 hermetically connects the injection opening and the first mating portion 311.

In a specific embodiment of this application, still referring to FIG. 5 and FIG. 8, the adapter 30 includes the adapting body 310 and the valve body 313, where the adapting body 310 has the first mating portion 311 and the second mating portion 312, the first mating portion 311 is configured to mate with the injection opening of the battery cell 20, the second mating portion 312 is configured to mate with the gas detection apparatus 40, and the gas flow passage a is constructed within the adapting body 310, the gas flow passage a running through the first mating portion 311 and the second mating portion 312 and being configured for gas to flow from the injection opening to the gas detection apparatus 40. The gas flow passage a includes the first passage a1, the second passage a2, and the mounting cavity a3. The first passage a1 runs through the first mating portion 311, the second passage a2 runs through the second mating portion 312, and the mounting cavity a3 connects the first passage a1 and the second passage a2. The valve body 313 is at least partially movably disposed in the mounting cavity a3. The first passage a1 and the second passage a2 run through two intersecting inner walls of the mounting cavity a3, respectively, one of the two inner walls is located in the moving direction of the valve body 313 and can be hermetically connected with the valve body 313 to turn off the gas flow passage a, and the other is spaced apart from the valve body 313. In this way, when the valve body 313 is controlled to move, a portion thereof located in the mounting cavity a3 can open or close the first passage a1 or the second passage a2, so as to turn on or off the gas flow passage a.

With the foregoing adapter 30, since the valve body 313 of the adapter 30 can be controlled to switch to the state of turning off the gas flow passage a, only the adapter 30 is needed on the battery cell 20 during transportation of the battery cell 20 for testing, and no gas detection apparatus 40 needs to be connected to ensure the gas tightness of the battery cell 20 for testing, so that it is more convenient to transport the battery cell 20.

According to some embodiments of this application, another aspect of this application further provides a testing apparatus, including a gas detection apparatus 40 and the adapter 30 according to any of the foregoing embodiments, where the gas detection apparatus 40 includes a connection tube 41 and a detector that are connected, the connection tube 41 is configured to mate with a second mating portion 312, the detector is configured to obtain characteristic information about gas flowing through the connection tube 41, and the characteristic information includes gas pressure information and/or gas composition information. The testing apparatus has all beneficial effects of the foregoing embodiments. Details are not repeated herein.

Figure 6:
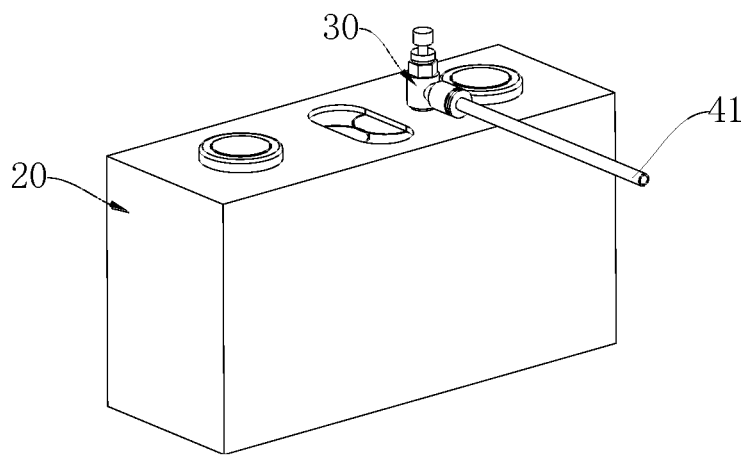
FIG. 6 is a use state diagram of the adapter shown in FIG. 4.
Figure 7:
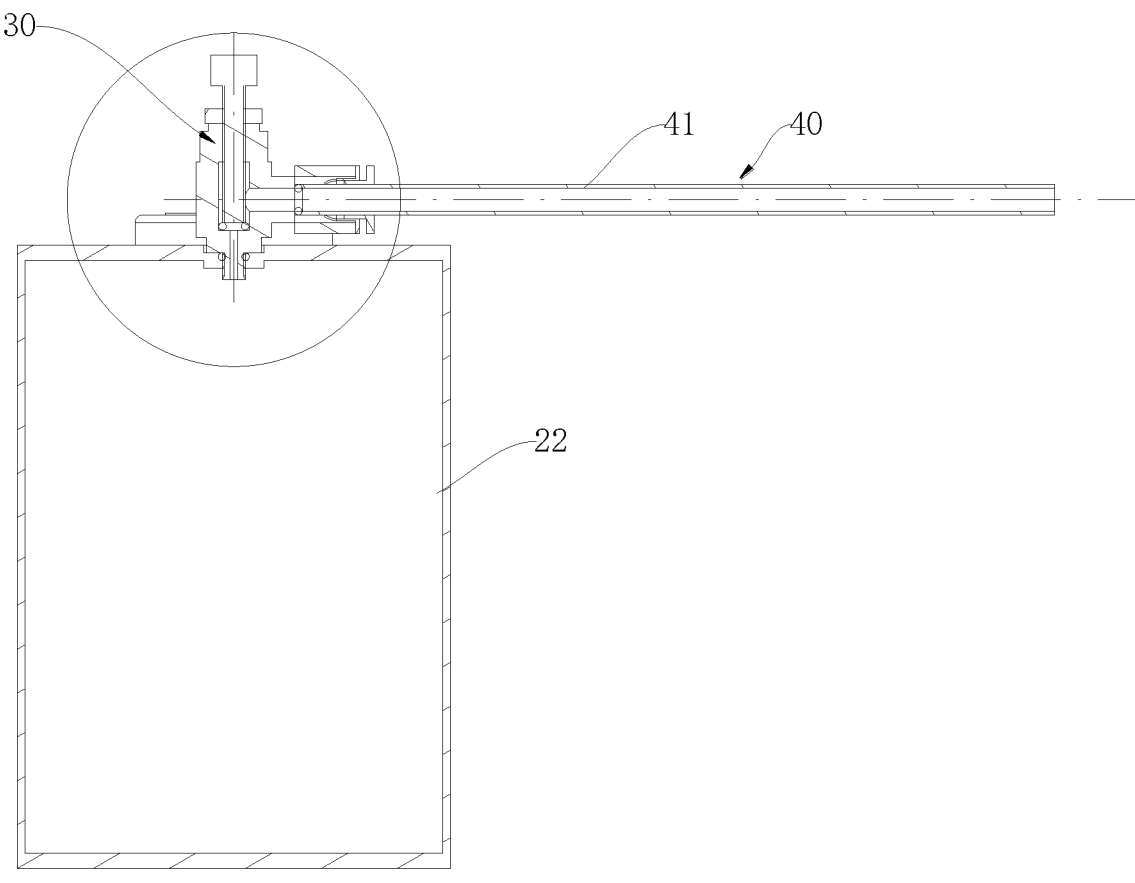
FIG. 7 is a cross-sectional view of the structure shown in FIG. 6.

During testing, still referring to FIG. 6 and FIG. 7, the first mating portion 311 of the adapter 30 is mated to the injection opening of the battery cell 20, and the second mating portion 312 of the adapter 30 is mated to the gas detection apparatus 40. During testing, the gas generated inside the battery cell 20 enters the gas detection apparatus 40 through the gas flow passage a in the adapter 30 for detection and analysis by the gas detection apparatus 40.

When the detector includes a pressure sensor, it can detect the pressure of the gas. When the detector includes a composition analyzer, it can detect the compositions of the gas.

In some embodiments, grease is adhered to the wall of the connection tube 41. The grease occupies the space inside the connection tube 41 so that characteristic information of a small amount of gas flowing through the connection tube 41 can be detected by the detector. The space of the connection tube 41 has little influence on the pressure inside the battery cell 20, and air pressure inside the connection tube 41 can be closer to the original air pressure environment inside the battery cell 20, which can improve the detection accuracy.

In some embodiments, the grease is silicone oil, which has good adhesion, will not fall off the wall, and is more likely to adhere to the wall of the connection tube 41.

According to some embodiments of this application, another aspect of this application further provides a battery cell 20, where the battery cell 20 includes a housing 22 and the adapter 30 according to any of the foregoing embodiments, the housing 22 has an injection opening, and a first mating portion 311 is mated to the injection opening. The battery cell 20 has all beneficial effects of the foregoing embodiments. Details are not repeated herein.

Figure 9:
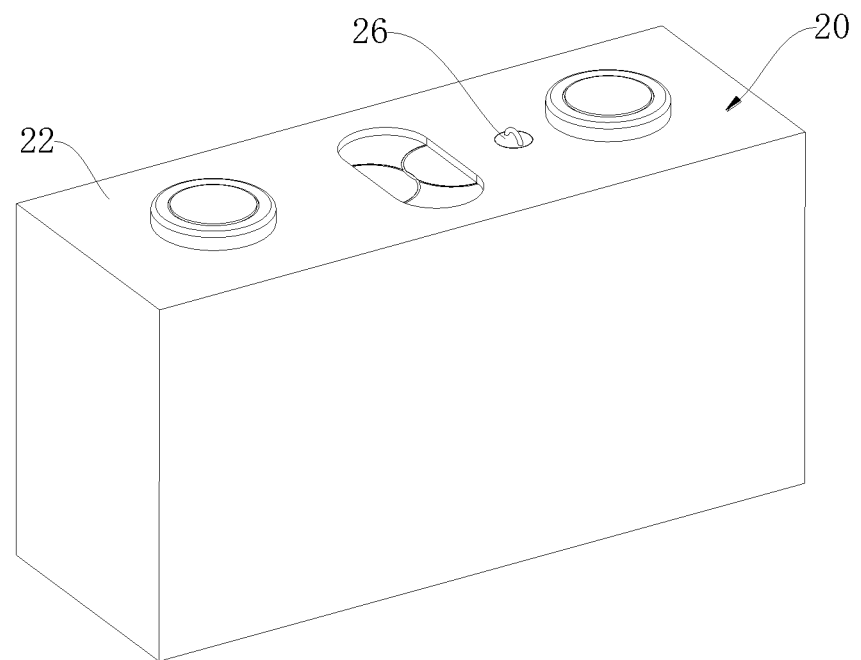
FIG. 9 is a schematic structural diagram of a battery cell according to some embodiments of this application.

In some embodiments, referring to FIG. 9, the battery cell 20 further includes a sealing nail 26, and a selected one of the first mating portion 311 and the sealing nail 26 is threadedly connected to the injection opening. When there is no need to test the battery cell 20, the sealing nail 26 may be used for threadedly connecting to and sealing the injection opening. When testing is required, the first mating portion 311 of the adapter 30 may be used for threadedly connecting to the injection opening. Use of the threaded connection facilitates switching of the battery cell 20 between testing and non-testing cases.

According to some embodiments of this application, another aspect of this application further provides a battery, the battery including the foregoing battery cell 20. The battery has all beneficial effects of the foregoing embodiments. Details are not repeated herein.

According to some embodiments of this application, another aspect of this application further provides an electric apparatus, including the foregoing battery. The electric apparatus has all beneficial effects of the foregoing embodiments. Details are not repeated herein.

Technical features in the foregoing embodiments may be combined in any way. For brevity of description, possible combinations of the technical features in the foregoing embodiments are not all described. However, as long as there is no contradiction among combinations of these technical features, all the combinations should be considered within a range recorded in this specification.

The foregoing embodiments only represent several implementations of this application, and descriptions thereof are specific and detailed, but should not be construed as a limitation on the patent scope of this application. It should be noted that those of ordinary skill in the art may further make several modifications and improvements without departing from the concept of this application, and these modifications and improvements also fall within the protection scope of this application. Therefore, the protection scope of this application should be subject to the appended claims.

What is claimed is:

1. An adapter, comprising:
an adapting body having a first mating portion and a second mating portion, wherein the first mating portion is configured to mate with an injection opening of a battery cell, the second mating portion is configured to mate with a gas detection apparatus, and a gas flow passage is constructed within the adapting body, the gas flow passage running through the first mating portion and the second mating portion and being configured for gas to flow from the injection opening to the gas detection apparatus; and
a valve body constructed to be movably disposed on the adapting body and movable relative to the adapting body when controlled to switch between states of turning on and off the gas flow passage;
wherein the gas flow passage comprises a first passage and a second passage, the first passage runs through the first mating portion, and the second passage runs through the second mating portion.

2. The adapter according to claim 1, wherein:
the gas flow passage further comprises a mounting cavity wherein, the mounting cavity connects the first passage and the second passage; and
the valve body is at least partially disposed in the mounting cavity and is constructed to be capable of switching between an off state and an on state when moving relative to the mounting cavity, wherein the valve body in the off state blocks the first passage and/or the second passage and the valve body in the on state is away from both the first passage and the second passage.

3. The adapter according to claim 2, wherein:
the first passage and the second passage run through two intersecting inner walls of the mounting cavity, respectively; and
the valve body is constructed to be movable relative to the mounting cavity when controlled, with one of the two inner walls located in a moving direction of the valve body and the other spaced apart from the valve body.

4. The adapter according to claim 3, further comprising:

a sealing member, wherein the sealing member is disposed in the mounting cavity, and the sealing member is capable of hermetically connecting the valve body with the inner wall in the moving direction of the valve body.

5. The adapter according to claim 1, wherein the gas flow passage comprises a mounting hole, wherein the mounting hole is formed in the second mating portion, and the mounting hole is configured to be sleeved around the gas detection apparatus.

6. The adapter according to claim 5, wherein the second mating portion is provided with an engaging member, the engaging member has an engaging hole, the engaging hole is coaxially connected to the mounting hole, and the engaging hole is constructed to be capable of being sleeved around the gas detection apparatus.

7. The adapter according to claim 6, wherein the engaging member is constructed to be capable of being extruded by the gas detection apparatus in the engaging hole to allow elastic deformation in a radial direction of the engaging hole to clamp the gas detection apparatus.

8. The adapter according to claim 7, wherein the engaging member comprises a clamp, wherein the clamp is enclosed to form the engaging hole, the clamp is hermetically connected to the second mating portion, an axial end of the clamp extends into the mounting hole, and a first elastic arm is provided on an end portion of the axial end, the first elastic arm being capable of undergoing elastic deformation in a radial direction of the engaging hole.

9. The adapter according to claim 8, wherein the engaging member further comprises an expansion sleeve, wherein the expansion sleeve is constructed to be capable of being movably sleeved in the engaging hole in an axial direction of the engaging hole, the expansion sleeve has a mating hole, the mating hole is coaxially disposed with the engaging hole, the mating hole is configured to mate with the gas detection apparatus, and the first elastic arm is squeezed at a position in a movement path of the expansion sleeve.

10. The adapter according to claim 5, further comprising:

a sealing member, the sealing member is disposed in the mounting hole, and the sealing member is configured to be capable of hermetically connecting the gas detection apparatus and the gas flow passage.

11. The adapter according to claim 10, wherein the gas flow passage further comprises an intermediate hole, the intermediate hole is formed in the second mating portion, the intermediate hole is coaxially connected to the mounting hole, the mounting hole has an inner side wall, the intermediate hole runs through the inner side wall, and the sealing member is disposed in the inner side wall and provided around the intermediate hole.

12. The adapter according to claim 1, wherein the first mating portion is removably connected to the injection opening.

13. The adapter according to claim 12, wherein the first mating portion is threadedly connected to the injection opening.

14. The adapter according to claim 12, further comprising:

a sealing member, the sealing member being configured to hermetically connect the first mating portion and the injection opening.

15. A testing apparatus, comprising:

the adapter according to claim 1; and a gas detection apparatus, comprising a connection tube and a detector that are connected, wherein the connection tube is configured to mate with the second mating portion, the detector is configured to obtain characteristic information about gas flowing through the connection tube, and the characteristic information comprises gas pressure information and/or gas composition information.

16. The testing apparatus according to claim 15, wherein grease is adhered to a wall of the connection tube.

17. A battery cell, comprising:

a housing; and the adapter according to claim 1;

wherein the housing has an injection opening, and the first mating portion is mated to the injection opening.

18. The battery cell according to claim 17, further comprising:

a sealing nail;

wherein one of the first mating portion and the sealing nail is threadedly connected to the injection opening.

19. A battery, comprising the battery cell according to claim 17.

20. An electric apparatus, comprising the battery according to claim 19.

* * * * *